(12) United States Patent
Coyle et al.

(10) Patent No.: US 9,511,399 B2
(45) Date of Patent: Dec. 6, 2016

(54) IN SITU ALKALINE HYDROLYSIS OF SUBSURFACE CONTAMINANTS USING GASEOUS REACTANTS

(71) Applicants: Charles G. Coyle, Omaha, NE (US); Victor F. Medina, Clinton, MS (US); Scott A. Waisner, Vicksburg, MS (US); Chung-Rei Mao, Omaha, NE (US)

(72) Inventors: Charles G. Coyle, Omaha, NE (US); Victor F. Medina, Clinton, MS (US); Scott A. Waisner, Vicksburg, MS (US); Chung-Rei Mao, Omaha, NE (US)

(73) Assignee: The United States of America as Represented by The Secretary of The Army, Washington, DC (US)

(*) Notice: Subject to any disclaimer, the term of this patent is extended or adjusted under 35 U.S.C. 154(b) by 0 days.

(21) Appl. No.: 14/692,210

(22) Filed: Apr. 21, 2015

(65) Prior Publication Data

US 2016/0311001 A1 Oct. 27, 2016

(51) Int. Cl.
| | | |
|---|---|---|
| *B09C 1/00* | (2006.01) | |
| *B09C 1/08* | (2006.01) | |
| *C02F 1/66* | (2006.01) | |
| *G01N 33/24* | (2006.01) | |
| *C02F 103/06* | (2006.01) | |

(52) U.S. Cl.
CPC ............ *B09C 1/08* (2013.01); *B09C 1/002* (2013.01); *C02F 1/66* (2013.01); *G01N 33/24* (2013.01); *B09C 2101/00* (2013.01); *C02F 2103/06* (2013.01); *C02F 2305/00* (2013.01)

(58) Field of Classification Search
CPC ............................. B29C 2101/00; B29C 1/08
See application file for complete search history.

(56) References Cited

U.S. PATENT DOCUMENTS

| | | | | |
|---|---|---|---|---|
| 5,384,048 A | * | 1/1995 | Hazen ............... | B09C 1/002 210/605 |
| 5,560,737 A | * | 10/1996 | Schuring ............ | B09C 1/00 166/246 |

* cited by examiner

*Primary Examiner* — John Kreck
(74) *Attorney, Agent, or Firm* — Brian C. Jones

(57) ABSTRACT

The present invention includes methods and a system for treating a mass of contaminated media using ammonia. The methods include determining the amount of ammonia required for treatment using various calculation methods and combining the ammonia with air or another carrier gas to create a gas mixture. The methods and system utilize at least one injection well inserted into the contaminated media to deliver the gas mixture over a period ranging from approximately 1 week to approximately 8 weeks.

19 Claims, 3 Drawing Sheets

US 9,511,399 B2

IN SITU ALKALINE HYDROLYSIS OF SUBSURFACE CONTAMINANTS USING GASEOUS REACTANTS

STATEMENT OF GOVERNMENT INTEREST

The invention was supported, in part, by funding from the Department of Defense Environmental Security Technology Certification Program (ESTCP), and from the Environmental Protection Agency (EPA). The United States Government has certain rights in the invention.

BACKGROUND

1. Field of Invention

This invention relates to the field of hydraulic and earth engineering, and more specifically to in situ contaminant removal or stabilization.

2. Detailed Description of Prior Art

Alkaline hydrolysis is a process for treatment of contaminated soil that involves raising pH levels to cause the contaminant to break down. This process has been successfully used for contaminants located primarily relatively close to the surface. However, alkaline hydrolysis has been unsuitable for treating contaminants trapped at intermediate and deeper levels of soil.

Liquid chemical applications, designed to penetrate the subsurface, flow downward through narrow cracks, crevices, and high-permeability channels present in soil. The liquid chemical becomes concentrated in some areas and bypasses large portions of the soil in others. High concentrations of alkaline materials may render drinking water unsafe and cause injury or damage to humans, animals and crops.

There is an unmet need in the art for a controlled method of alkaline hydrolysis that is effective for eradicating subsurface soil contamination without causing additional environmental damage.

SUMMARY OF THE INVENTION

In one embodiment of the invention, a method for treating a mass of contaminated media includes the steps of removing a sample of the contaminated media and testing the sample to determine a current pH level $P_A$ and a current lime buffering capacity $B_L$ of the contaminated media, then calculating a quantity M of the ammonia needed for treatment of the contaminated media using the equation $$M = (P_D - P_A) * A_C * F * B_L$$

wherein $P_D$ is a desired pH of the contaminated media, $A_C$ is a constant value of approximately 0.34 milligrams of the ammonia per milligram of calcium carbonate, F is a safety factor of approximately 10.4. The method then inserts the at least one injection well into the contaminated media at the distribution, creates a gas mixture by combining the quantity M of the ammonia with air and delivers the gas mixture over a period ranging from approximately 1 week to approximately 8 weeks.

In another embodiment of the invention, a method for treating a mass of contaminated media includes the steps of removing a sample of the contaminated media, administering a known quantity $M_T$ of ammonia to the sample of the contaminated media by injecting the known quantity of ammonia through the sample of the contaminated media, testing the sample of the contaminated media to determine a current pH $P_A$ of the sample of the contaminated media and calculating a quantity of ammonia M needed for treatment of the contaminated media using the equation $$M = \frac{M_T * M_C * (P_D - P_A)}{M_S * (P_D - P_A)}$$

wherein $M_C$ is a mass of the contaminated media to be treated, $P_D$ is a desired pH of the contaminated media, and $M_S$ is a mass of the sample of contaminated media. The method then inserts the at least one injection well into the contaminated media, creates a gas mixture of the ammonia with air and/or a carrier gas and delivers the gas mixture over a period ranging from approximately 1 week to approximately 8 weeks.

In another embodiment of the invention, a system for treating contaminated media includes an air source, an ammonia source, at least one injection well and a control cabinet. The air source contains air. The ammonia source contains a quantity M of the ammonia required to treat the contaminated media, the quantity M calculated using the equation $$M = (P_D - P_A) * A_C * F * B_L$$

wherein $P_D$ is the desired pH of the contaminated media, $P_A$ is the current pH of the contaminated media, $A_C$ is a constant value of approximately 0.34 milligrams of the ammonia per milligram of calcium carbonate, F is a safety factor of approximately 10.4 and $B_L$ is a lime buffering capacity of the contaminated media expressed in units of milligrams of calcium carbonate per kilogram of the contaminated media per unit of pH. The control cabinet is connected between the air source, the ammonia source and the at least one injection well.

TERMS OF ART

As used herein, the term "groundwater" means water occurring below the ground surface.

As used herein, the term "lime buffer capacity" means the amount of media acidity that must be neutralized to raise media pH by one unit, expressed in units of milligrams of calcium carbonate per kilogram of media per unit of pH.

As used herein, the term "perched water" means groundwater occurring in a saturated zone separated from a main body of groundwater by unsaturated rock, sediments or soil.

As used herein, the term "saturated" or "saturation" means a state wherein additional water cannot be absorbed.

As used herein, the term "vadose zone" means a zone of soil extending from the ground surface to the water table.

DETAILED DESCRIPTION OF INVENTION

Figure 1:
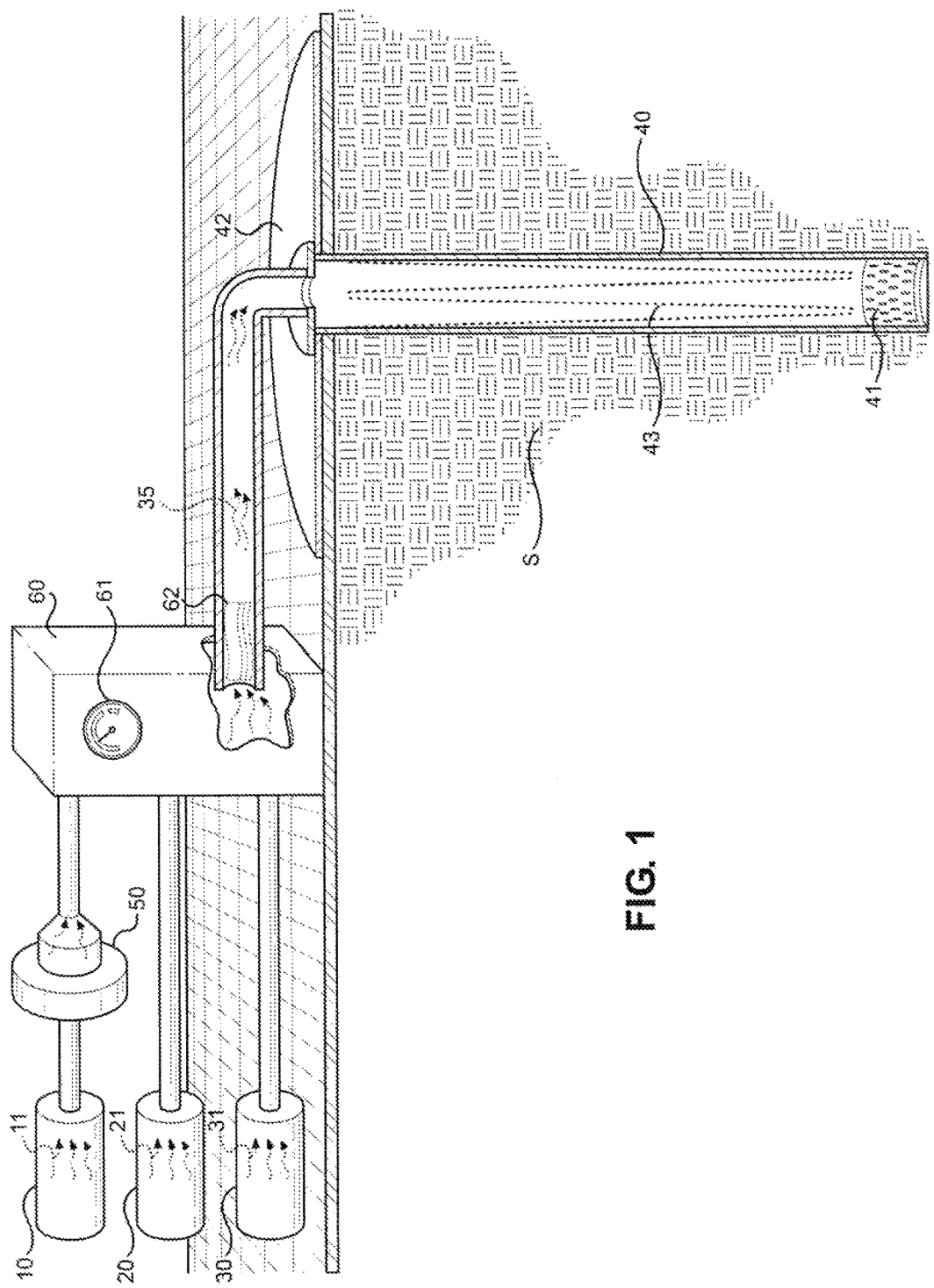
FIG. 1 illustrates an exemplary system for raising the pH of contaminated media to promote in situ alkaline hydrolysis of contaminated media.

FIG. 1 illustrates an exemplary system 100 for promoting in situ alkaline hydrolysis of contaminated media S. System 100 includes an air source 10 providing air 11, an optional carrier gas source 20 providing an optional carrier gas 21, an ammonia source 30 providing ammonia 31 to create a gas mixture 35, an injection well 40, an optional blower 50 and a control cabinet 60.

Air source 10 provides air 11. Air 11 conveys carrier gas 21, ammonia 31 and other gases in gas mixture 35 to injection well 40. In the exemplary embodiment, air source 11 is a compressor and compressed air tank. In another embodiment, blower 50 propels air 11 through system 100.

Optional carrier gas source 20 contains a carrier gas 21 including, but not limited to, nitrogen or other gasses. Carrier gas source 20 supplies carrier gas 21 as compressed gas or refrigerated liquid, or through generation membrane or pressure swing adsorption processes. Carrier gas 21 provides an additional or alternate gas to combine with ammonia 31 to create gas mixture 35 if air 11 contains unacceptable levels of oxygen or other components that could create an explosion hazard or dangerous conditions.

Ammonia source 30 for ammonia 31 may be a tank of liquid anhydrous ammonia, or a tank of compressed gaseous ammonia. In one embodiment, in gas mixture 35 combining ammonia 31 with air 11 and/or carrier gas 21, ammonia 31 makes up approximately 4% to approximately 14% of gas mixture 35. In another embodiment, ammonia 31 concentrations ranging from approximately 15% to approximately 28% may be used if carrier gas 21 is substituted for air 11, to mitigate the risk of creating an explosive gas mixture. In another embodiment, in gas mixture 35 combining ammonia 31 with air 11 and/or carrier gas 21, ammonia 31 makes up more than approximately 28% of gas mixture 35. The concentration of this embodiment may be used if there are barriers, geological features, or climactic conditions which mitigate the risk of ammonia 31 (or transformation products) migrating to groundwater.

Injection well 40 is a hollow tubular insert approximately 1 inch to 4 inches in diameter, constructed from polymers, metals or other rigid materials. Injection well 40 extends from the surface of contaminated media S to a given treatment depth to allow delivery of gas mixture 35, and may extend through multiple different types of contaminated media S, such as both soil and groundwater. One embodiment utilizes a single injection well 40, while other embodiments include multiple injection wells 40. In embodiments using multiple injection wells 40, the distribution of injection wells 40 depends on a pneumatic permeability K of contaminated media S.

Injection well 40 has solid sidewalls except for at least one perforated section 41. Perforated section 41 includes apertures that allow delivery of gas mixture 35 from injection well 40 into contaminated media S. If contaminated media is located in a multiple subsurface layers, then injection well 40 may include more than one perforated section 41. For example, if contaminated media S were located at depths of 10-12 feet and 20-24 feet, then injection well 40 would include first and second perforated sections 41. A first perforated section 41 would begin at a location 10 feet from a first end and extend 2 feet along injection well 40. A second perforated section 41 would begin at a location 20 feet from an upper end and extend 4 feet along injection well 40.

In one embodiment, injection well 40 also includes a surface cover 42. Surface cover 42 is impermeable to gas and prevents any delivered gas mixture 35 from escaping up through contaminated media S and into the atmosphere, particularly during delivery at a shallow depth.

In one embodiment, injection well 40 also includes at least one resistive heating element 43 located on an outer surface of injection well 40. Resistive heating element 43 allows heating of contaminated media S to temperatures ranging from approximately 20 degrees Celsius to approximately 70 degrees Celsius. Because ammonia 31 is hydrophilic, and has a very high solubility in water, the water content of contaminated media S influences the radial distribution of ammonia 31 from injection well 40. Increasing water content reduces the radial distribution of ammonia 31. Heating contaminated media S can decrease its water content.

Blower 50 may be used to convey gas mixture 35 to injection well 40. Blower 50 propels air 11 through system 100, allowing air 11 to convey carrier gas 21, ammonia 31 and other gases of gas mixture 35 to injection well 40. Due to this function, blower 50 must be located "upstream" of carrier gas source 20 and ammonia source 30, or of a piping junction where carrier gas source 21 and ammonia source 31 are introduced. In certain embodiments, blower 50 also heats air 11.

Control cabinet 60 incorporates at least one flow meter 61 and a static mixer 62. Flow meter 61 allows a user to regulate the flow of air 11, carrier gas 21, ammonia 31 and other gases to ensure gradual delivery of gas mixture 35. Static mixer 62 evenly combines air 11, carrier gas 21 and ammonia 31 to create gas mixture 35.

Figure 2A:
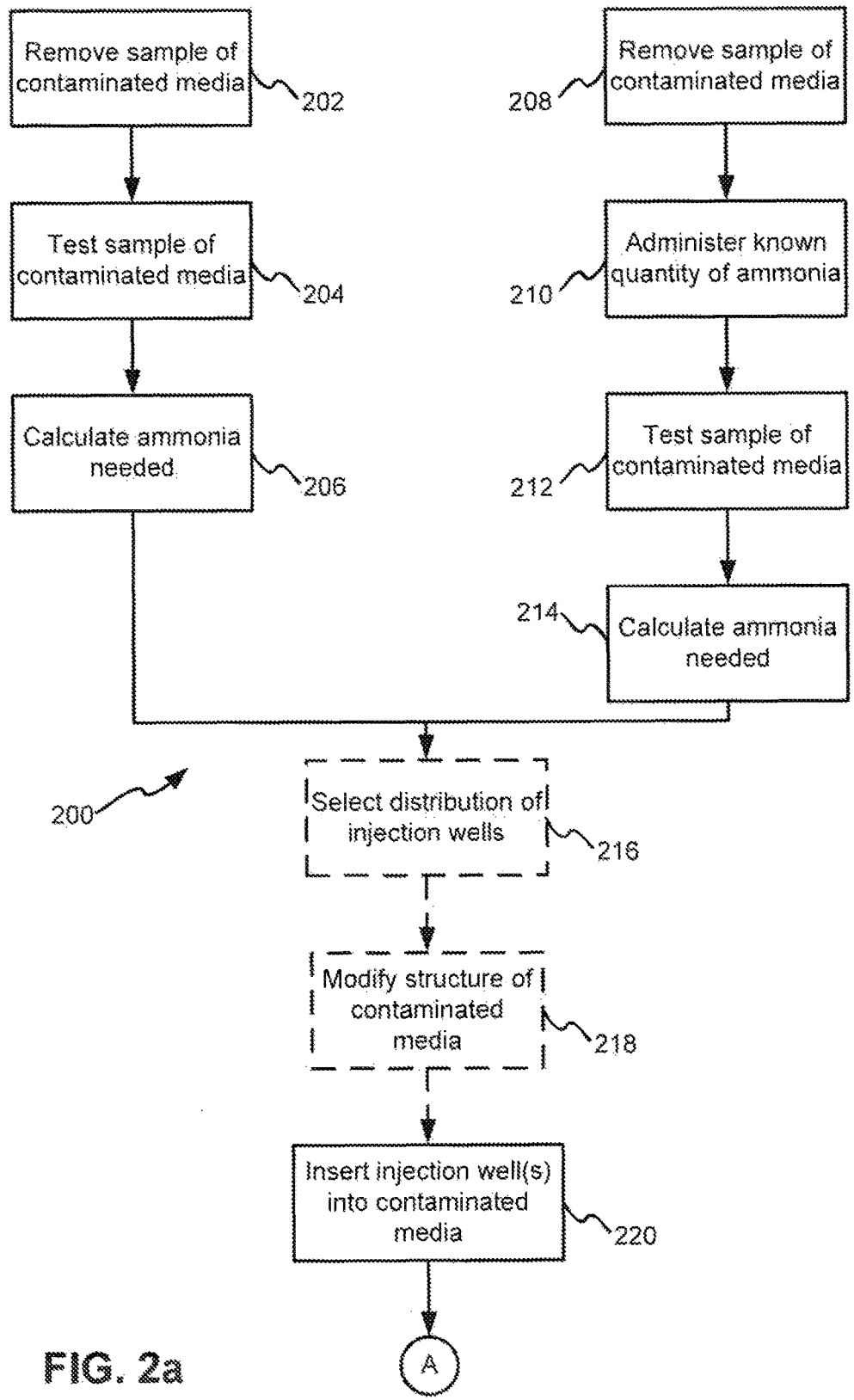
FIGS. 2a and 2b illustrate a flowchart of an exemplary method for raising the pH of contaminated media to promote alkaline hydrolysis reactions.
Figure 2B:
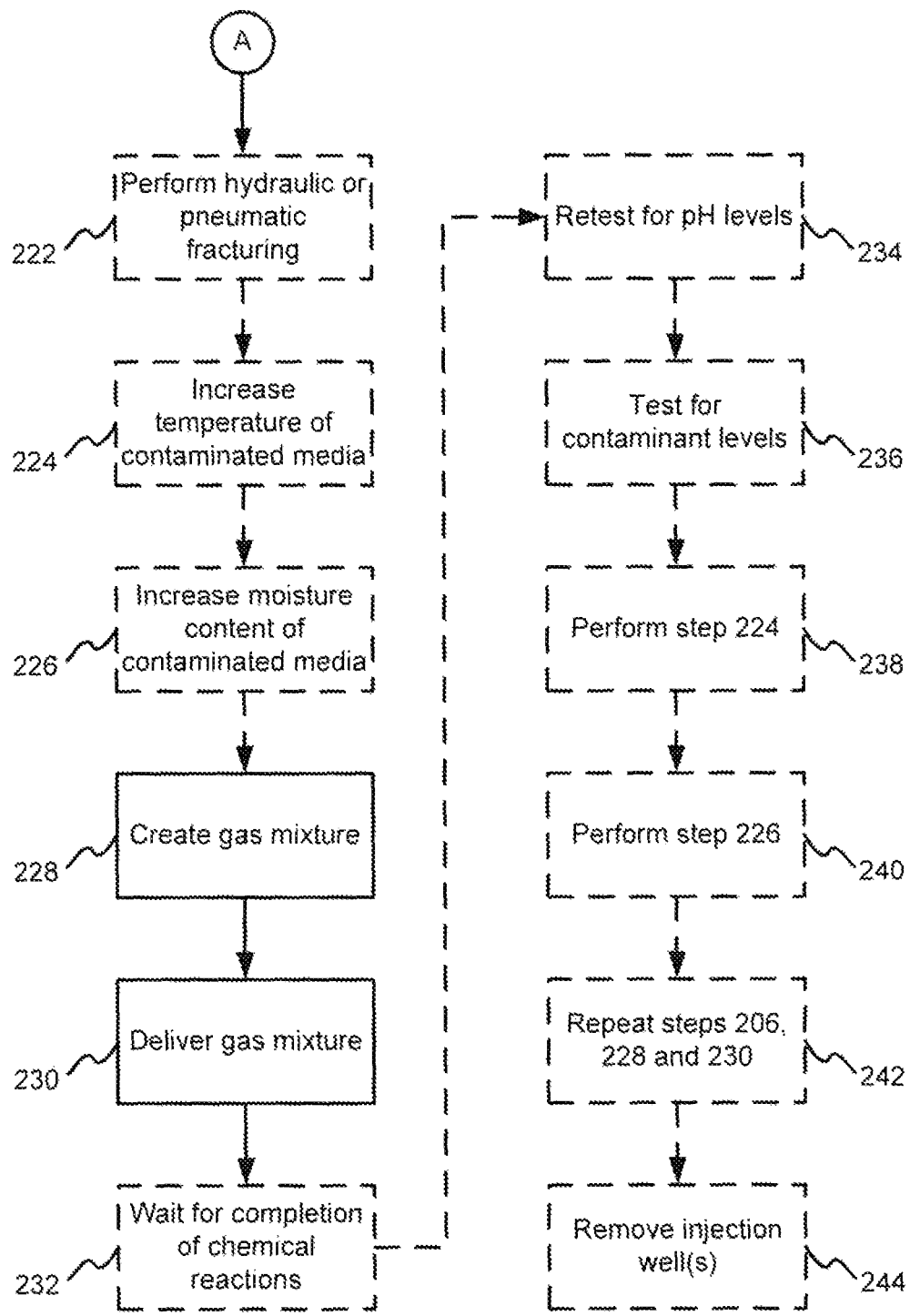

FIGS. 2a and 2b illustrate an exemplary method 200 for raising the pH of contaminated media S to promote alkaline hydrolysis reactions. Method 200 raises the pH of contaminated media S such as soils, groundwater, perched water and sediments. In one embodiment, contaminated media S is unsaturated soil. In another embodiment, contaminated media S is soil in the vadose zone. In alternate embodiments, the contaminated media S is saturated soils and sediments.

In steps 202 to 206, method 200 determines a quantity M of ammonia 21 required to raise the pH of contaminated media S.

In step 202, method 200 removes a sample of contaminated media.

In step 204, method 200 tests the sample of contaminated media S to determine current pH $P_A$ and lime buffering capacity $B_L$.

In step 206, method 200 calculates quantity M of ammonia 21 needed using the equation $$M=(P_D-P_A)*A_C*F*B_L$$

wherein $P_D$ is the desired pH of contaminated media S, $A_C$ is a constant value of approximately 0.34 milligrams of ammonia per milligram of calcium carbonate and F is a safety factor of approximately 10.4.

In steps 208 to 214, method 200 determines quantity M of ammonia 21 required to raise the pH of contaminated media S using an alternate method.

In step 208, method 200 removes a sample of contaminated media S. In one embodiment, the sample of contaminated media S is removed to a test column.

In step 210, method 200 administers a known quantity $M_T$ of ammonia 21 to the sample of contaminated media S by injecting known quantity $M_T$ of ammonia 21 into the sample of contaminated media S. In one embodiment, injection is performed through the test column at a known flow rate and temperature.

In step 212, method 200 tests the sample of contaminated media S to determine current pH $P_A$ after treatment.

In step 214, method 200 calculates the quantity M of ammonia 21 needed for treatment using the equation $$M = \frac{M_T * M_C * (P_D - P_A)}{M_S * (P_D - P_A)}$$

wherein $M_C$ is the mass of contaminated media S and $M_S$ is the mass of the sample of contaminated media S.

In optional step 216, when method 200 utilizes a plurality of injection wells 40, method 200 selects the distribution of injection wells 40 based on pneumatic permeability K of contaminated media S, calculated using the equation $$K = \frac{Q * P^* * \mu}{\pi * b} \frac{\ln(r_2/r_1)}{P_1^2 - P_2^2}$$

wherein Q is the volumetric flow rate, P* is the pressure at the point of flow measurement, p is the viscosity of air, b is the vertical thickness of contaminated media S, $r_1$ and $r_2$ are the distance to observation points and $P_1$ and $P_2$ are the absolute pressures at observation points.

In optional step 218, method 200 modifies the structure of contaminated media S to allow insertion of at least one injection well 40 into contaminated media S as determined in step 216. In one embodiment, method 200 removes a portion of contaminated media S to form a void in the contaminated media sized to accept injection well 40. This removal can utilize hand tools, an auger drill or other power tools. The void will have a diameter at least as large as the outer diameter of injection well 40 and a depth sufficient to align perforated section 41 with the full thickness of contaminated media S.

In step 220, method 200 inserts at least one injection well 40 into contaminated media S at intervals determined in step 216.

In optional step 222, method 200 performs hydraulic or pneumatic fracturing to increase the permeability of contaminated media S.

In optional step 224, method 200 may increase the temperature of contaminated media S. In one embodiment, this step delivers heated gas, such as steam or heated air 11, to contaminated media S through injection well 40. In another embodiment, the user runs electric current through at least one resistive heating element 43 located on an outer surface of injection well 40. The final temperature of contaminated media S ranges from approximately 20 degrees Celsius to approximately 70 degrees Celsius.

In optional step 226, method 200 may increase the moisture content of contaminated media S. This step delivers humidified gas, such as steam, or air 11 or carrier gas 21 humidified by passage through water spray or by bubbling through a water vessel. The final moisture content of contaminated media S may range from approximately 5% to any point below media saturation.

In step 228, method 200 creates gas mixture 35 by combining ammonia 31 with air 11 and/or carrier gas 21. Depending on the embodiment, ammonia 21 makes up approximately 4% to approximately 14%, approximately 14% to approximately 28% or more than approximately 28% of gas mixture 35.

In step 230, method 200 delivers gas mixture 35. Delivery may occur over a period ranging from approximately 1 week to approximately 8 weeks. In certain embodiments, step 230 may be performed simultaneously with step 224 and/or step 226.

In optional step 232, method 200 waits for a period of approximately 2 weeks to approximately 6 weeks for completion of any chemical reactions in contaminated media S.

In optional step 234, method 200 retests for pH levels.

In optional step 236, method 200 tests for contaminant levels.

In optional step 238, method 200 performs step 224 to heat contaminated media S and/or reduce the moisture content in contaminated media S. In certain embodiments of method 200, treatment of a large area may follow treatment of a small area. Heating contaminated media S allows this sequence using the same distribution of injection wells 40.

In optional step 240, method 200 performs step 226 to increase the moisture content in contaminated media S. In certain embodiments of method 200, treatment of a small area may follow treatment of a large area. Increasing the moisture content of contaminated media S allows this sequence using the same distribution of injection wells 40.

In optional step 242, method 200 repeats performance of steps 206, 228 and 230. In certain embodiments of method 200, treatment of contaminated media S may be separated into multiple iterative treatments using smaller amounts of ammonia 31 to allow more precise control over the process or to prevent the build-up of dangerous chemicals, such as nitrates.

In optional step 244, method 200 removes injection well 40. If method 200 does not remove injection well 40, then injection well 40 remains in place and is abandoned.

It will be understood that many additional changes in the details, materials, procedures and arrangement of parts, which have been herein described and illustrated to explain the nature of the invention, may be made by those skilled in the art within the principle and scope of the invention as expressed in the appended claims.

It should be further understood that the drawings are not necessarily to scale. Instead, emphasis has been placed upon illustrating the principles of the invention. Like reference numerals in the various drawings refer to identical or nearly identical structural elements. Moreover, the term "approximately" as used herein may be applied to modify any quantitative representation that could permissibly vary without resulting in a change in the basic function to which it is related. Furthermore, all percentages referred to herein are percentages by volume.

What is claimed is:

1. A method for treating a mass of contaminated media, comprising the steps of:

removing a sample of said contaminated media;

testing said sample to determine a current pH level $P_A$ and a current lime buffering capacity $B_L$ of said contaminated media;

calculating a quantity M of said ammonia needed for treatment of said contaminated media using the equation $$M = (P_D - P_A) * A_C * F * B_L$$

wherein $P_D$ is a desired pH of said contaminated media, $A_C$ is a constant value of approximately 0.34 milligrams of said ammonia per milligram of calcium carbonate, F is a safety factor of approximately 10.4;

inserting said at least one injection well into said contaminated media;

creating a gas mixture by combining said quantity M of said ammonia with air and/or carrier gas; and delivering said gas mixture over a period ranging from approximately 1 week to approximately 8 weeks.

2. The method of claim 1, further comprising the step of performing hydraulic or pneumatic fracturing of said contaminated media before delivering said gas mixture.

3. The method of claim 1, further comprising the step of modifying a structure of said contaminated media to allow insertion of said at least one injection well before inserting said at least one injection well.

4. The method of claim 1, wherein said at least one injection well comprises a plurality of injection wells.

5. The method of claim 4, wherein said method further comprises the step of selecting a distribution of said plurality of injection wells based on a pneumatic permeability K of said contaminated media calculated using the equation $$K = \frac{Q * P^* * \mu}{\pi * b} \frac{\ln(r_2/r_1)}{P_1^2 - P_2^2}$$

wherein Q is the volumetric flow rate, $P^*$ is the pressure at the point of flow measurement, $\mu$ is the viscosity of air, b is the vertical thickness of said contaminated media, $r_1$ and $r_2$ are the distance to observation points and $P_1$ and $P_2$ are the absolute pressures at observation points.

6. The method of claim 1, further comprising the step of increasing a temperature of said contaminated media.

7. The method of claim 6, wherein said temperature of said contaminated media increases to a final temperature ranging from approximately 20 degrees Celsius to approximately 70 degrees Celsius.

8. The method of claim 1, further comprising the step of increasing a moisture content of said contaminated media.

9. The method of claim 8, wherein said moisture content of said contaminated media increases to a final moisture content ranging from approximately 5% to a point below saturation of said contaminated media.

10. The method of claim 1, wherein said ammonia makes up approximately 4% to approximately 14% of said gas mixture.

11. The method of claim 1, wherein said ammonia makes up approximately 14% to approximately 28% of said gas mixture.

12. The method of claim 1, wherein said ammonia makes up more than approximately 28% of said gas mixture.

13. The method of claim 1, further comprising the step of waiting for a period of approximately 2 weeks to approximately 6 weeks for completion of any chemical reactions in said contaminated media.

14. The method of claim 1, further comprising the step of retesting said current pH level of said contaminated media.

15. The method of claim 1, wherein said contaminated media comprises soil.

16. The method of claim 15, wherein said soil is in the vadose zone.

17. The method of claim 1, wherein said contaminated media comprises groundwater.

18. The method of claim 17, wherein said groundwater is perched water.

19. A method for treating a mass of contaminated media, comprising the steps of:
  removing a sample of said contaminated media;
  administering a known quantity $M_T$ of ammonia to said sample of said contaminated media by injecting said known quantity of ammonia through said sample of said contaminated media;
  testing said sample of said contaminated media to determine a current pH $P_A$ of said sample of said contaminated media;
  calculating a quantity of ammonia M needed for treatment of said contaminated media using the equation $$M = \frac{M_T * M_C * (P_D - P_A)}{M_S * (P_D - P_A)}$$

wherein $M_C$ is a mass of said contaminated media to be treated, $P_D$ is a desired pH of said contaminated media, and $M_S$ is a mass of the sample of contaminated media;
  inserting said at least one injection well into said contaminated media;
  creating a gas mixture of said ammonia with air and/or carrier gas; and
  delivering said gas mixture over a period ranging from approximately 1 week to approximately 8 weeks.

* * * * *